US007163508B1

(12) United States Patent
Washington

(10) Patent No.: US 7,163,508 B1
(45) Date of Patent: Jan. 16, 2007

(54) LUBRICATING SEXUAL AID

(76) Inventor: Kathy L Washington, 4211 S. Mobile Cir. #C, Aurora, CO (US) 80013

( * ) Notice: Subject to any disclaimer, the term of this patent is extended or adjusted under 35 U.S.C. 154(b) by 72 days.

(21) Appl. No.: 11/004,728

(22) Filed: Dec. 3, 2004

(51) Int. Cl.
*A61F 5/00* (2006.01)

(52) U.S. Cl. ........................................................ 600/38

(58) Field of Classification Search ............ 600/38–41, 600/587, 842, 33–35; 128/897, 898; 604/187, 604/208, 218, 228, 236, 237, 249
See application file for complete search history.

(56) References Cited

U.S. PATENT DOCUMENTS

| | | | | |
|---|---|---|---|---|
| 1,699,590 A * | 1/1929 | Ireland | ........................ | 604/218 |
| 2,842,128 A * | 7/1958 | Hein, Jr. | ...................... | 604/227 |
| 4,919,149 A | 4/1990 | Stang | | |
| 4,921,487 A * | 5/1990 | Buffet et al. | ................ | 604/135 |
| 6,027,443 A * | 2/2000 | Nag | ............................ | 600/33 |
| 6,203,491 B1 | 3/2001 | Uribe | | |
| 6,350,230 B1 * | 2/2002 | Kontos | ........................ | 600/38 |
| 6,733,438 B1 | 5/2004 | Dann et al. | | |
| 6,749,557 B1 | 6/2004 | Garland | | |
| 2003/0171647 A1 | 9/2003 | Garland | | |

FOREIGN PATENT DOCUMENTS

| | | |
|---|---|---|
| GB | 1.403.799 | 8/1975 |
| WO | WO03/099189 | 12/2003 |

* cited by examiner

*Primary Examiner*—Samuel G. Gilbert
(74) *Attorney, Agent, or Firm*—Michael I. Kroll

(57) ABSTRACT

A lubricating insertable sexual aid comprising a shaft having a throughbore extending therethrough for retaining a lubricant therein. A head having an egress aperture extending through a tip thereof is removeably connected to a first end of the shaft. The aid further includes means received within the throughbore at an end opposite of the head for dispensing the lubricant. Upon insertion into an orifice and activation of the dispensing means, the dispensing means exerts a pressure on the lubricant thereby causing the lubricant to be output via the egress aperture and to be evenly distributed over an exterior surface of each of the head and shaft.

10 Claims, 10 Drawing Sheets

LUBRICATING SEXUAL AID

BACKGROUND OF THE INVENTION

1. Field of the Invention

The present invention relates generally to lubricating sexual aid devices and, more specifically, to a sexual aid having a hollow interior chamber for receiving a lubricating element, a syringe-like plunger member for pressurizing the lubricating element within the interior chamber for exit though a point of egress thereby releasing the lubricating element to an exterior portion of the sexual aid body.

2. Description of the Prior Art

There are other lubricating sexual aids devices known in the art. Typical of these is U.S. Pat. No. 4,919,149 issued to Michael A. Stang on Apr. 24, 1990.

Another patent was issued to Richard M. Uribe on Mar. 20, 2001 as U.S. Pat. No. 6,203,491. Yet another U.S. Pat. No. 6,350,230 was issued to George Vaslo Kontos on Feb. 26, 2002 and still yet another was issued on May 11, 2004 to Jeffrey Dann et al. as U.S. Pat. No. 6,733,438.

Another patent was issued to Lawrence B. Garland on Jun. 15, 2004 as U.S. Pat. No. 6,749,557. U.K. Patent No. GB 1 403 799 was issued to C. R. Bard Inc. on Aug. 20, 1975 and International Patent Publication No. WO 03/099189 was published on Dec. 4, 2003 to Bruno Pezzana.

U.S. Pat. No. 4,919,149

Inventor: Michael A. Stang

Issued: Apr. 24, 1990

A contraception and flavor delivery system (10) includes an extended tubular member (20) having a closed distal end (22) and an open proximal end (24). The contraception and delivery system (10) further includes a mechanism for flavor delivery (30) formed on an external surface of the tubular member (20). The mechanism for flavor delivery (30) includes at least one longitudinally extended tubular housing (40) having an open first end (42) and a closed second end (46) for containing a predetermined quantity of an ingestible flavored composition. The open first end (42) of tubular housing (40) is provided with a closure (44) adapted to release the ingestible flavored composition into a bodily orifice responsive to an external stimuli.

U.S. Pat. No. 6,203,491

Inventor: Richard M. Uribe

Issued: Mar. 20, 2001

An improved hands-free adult sexual apparatus or adult toy for use by women or men. The apparatus is secured onto the user, or the user's clothing or belt, in a harness-like assembly and is also partially restrained to a fixed object. In one embodiment, a dildo or other phallic device is secured to a supportive backing while elastic straps allow the user to comfortably utilize the invention. A restraining line partially secures movement of the dildo or phallic device while the user manipulates the elastic straps. In another embodiment, the phallic device has a lubricant chamber that is activated by a user controlled trigger to permit the user to add lubricant as desired to the phallic device. In another embodiment, the invention has instead a sheathing device for use by males.

U.S. Pat. No. 6,350,230

Inventor: George Vlasio Kontos

Issued: Feb. 26, 2002

A sexual aid device for producing sexual stimulation having an elongated upper member, an elongated lower member, a means for removably securing the upper and lower members together, a tube member, and a compression means for ejaculating liquid from the tube member. An upper end of the upper member has an aperture therethrough. The elongated lower member has a compartment therein for one or more batteries for powering the device. The tube member has a compressible liquid containment unit on a lower end thereof. A hollow neck member extends upward from the liquid containment unit, the hollow neck member being in fluid communication with the liquid containment unit. The neck member has an open upper end. During use the tube member is positioned inside the device such that the open upper end of the neck member is inserted in the aperture of the upper member. The compression means is configured and positioned to compress the liquid containment unit to thereby ejaculate liquid from the tube member. The device is preferably provided with a vibration means, a timing unit, and a heating element, all of which may be selectively used as needed when using the device to provide sexual stimulation. Methods of using the device are also provided.

U.S. Pat. No. 6,733,438

Inventor: Jeffrey Dann et al.

Issued: May 11, 2004

A female stimulation device comprising a resilient device body having a partially deformable tip portion, a flange and an intermediate side wall portion extending outwardly from the tip portion to the flange. In use, the tip portion is compressed to force air out of the device body and the flange is placed in contact with vaginal wall tissue so that the clitoris is encompassed by the device body. Release and restorative deformation of the tip portion causes a partial vacuum within the device body, which maintains the device in place and provides suction to the clitoris. The intermediate side wall portion is substantially non-deformable in response to deformation of the tip portion, as may be achieved with outwardly convex side walls, thereby preventing deleterious entrapment and compression of the clitoris. Pharmacologically active materials, such as vasoactive agents, substances, and medications, may be applied to the device for contact with the clitoris during use in order to further enhance female sexual function.

U.S. Pat. No. 6,749,557

Inventor: Lawrence B. Garland

Issued: Jun. 15, 2004

A sex aid system modified to be self lubricating, and including a hollow chamber for carrying lubricating fluid; and a mechanism for connecting the hollow chamber to the sex aid. The sex aid includes a surface portion intended to contact the external or internal surfaces of users or a user; and one or more hole at the surface portion in fluid contact with the connecting mechanism. In use, any lubricating fluid contained in the hollow chamber may traverse through the connecting mechanism and thence through the one or more hole to the surface portion of the sex aid to thereby render the sex aid self lubricating.

U.K. Patent Number G.B. 1 403 799

Inventor: C. R. Bard Inc.

Issued: Aug. 20, 1975

A catheter adapted for insertion into a body passage of restricted size, the catheter comprising a shaft with a distal tip and a proximal end, a main lumen extending within the shaft from a point adjacent the distal tip to the proximal end, and a lubrication system including an eye which is disposed close to the distal tip of the catheter.

International Patent Number W/O 03/099189

Inventor: Bruno Pezzana

Issued: Dec. 4, 2003

The sexual aid of the invention comprises a mechanical device (10) operated by a motor (50) and having an upper end (20') movable, by operating the motor (50), with a reciprocating to-and-fro movement imitating the reciprocating coital movement, the artificial penis (7) being fixable rigidly to said upper end (20') of the mechanical device (10). Specifically, the mechanical device (10) comprises an outer container part (30) of elongate tubular form, having an inner cylindrical chamber (3) into which said support part (20) is inserted and coupled telescopically in a manner able to slide in an axial direction. Moreover, the outer container part (30) encloses within its interior the operating motor (50), which is disposed to the rear of the support part (20), the outer container part (30) being substantially coaxial with the artificial penis (7).

While these lubricating sexual devices may be suitable for the purposes for which they were designed, they would not be as suitable for the purposes of the present invention, as hereinafter described.

SUMMARY OF THE PRESENT INVENTION

The present invention relates generally to lubricating sexual aid devices and, more specifically, to a sexual aid having a hollow interior chamber for receiving a lubricating element, a syringe-like plunger member for pressurizing the lubricating element within the interior chamber for exit though a point of egress thereby releasing the lubricating element to an exterior portion of the sexual aid body.

A primary object of the present invention is to provide a lubricating sexual aid that overcomes the shortcomings of the prior art.

Another, secondary object of the present invention is to provide a lubricating sexual aid that is insertable within an orifice of the human body.

Yet another object of the present invention is to provide a lubricating sexual aid having an interior chamber for retaining a lubricant therein.

Still another object of the present invention is to provide a lubricating sexual aid including an egress aperture to allow said lubricant to pass from said interior chamber onto an exterior surface of the aid.

An even further object of the present invention is to provide a lubricating sexual aid including a manually operable plunger mechanism for causing the lubricant to egress from the egress aperture.

Another object of the present invention is to provide an insertable lubricating sex aid that can be used without the user getting lubricant on their hands.

Still another object of the present invention is to provide an insertable lubricating sex aid wherein additional lubricant can be applied to the surface while in use.

Yet another object of the present invention is to provide an insertable lubricating sex aid that is economical because there is no wasted lubricant on the user's hands after application.

Still yet another object of the present invention is to provide an insertable lubricating sex aid that is convenient because there is no additional bottle of lubricant for subsequent application to the sexual aid.

Another object of the present invention is to provide an insertable lubricating sex aid that is refillable.

Yet another object of the present invention is to provide an insertable lubricating sex aid that is simple and easy to use.

Still yet another object of the present invention is to provide an insertable lubricating sex aid that is inexpensive to manufacture and operate.

Additional objects of the present invention will appear as the description proceeds.

Phallus-like sexual aids such as dildos have frequently been used throughout the ages to provide sexual stimulation to the user or the user's partner. However, the synthetic nature of these devices give them naturally dry surfaces that can be uncomfortable and cause irritation when inserted into a body cavity, particularly when the natural lubrication of the cavity is insufficient to relieve friction. There are other devices designed to lubricate similar type sex aids but the present invention overcomes the shortcomings of the prior art by providing a hands-free means of applying lubricant to the surface by means of a simple syringe-like plunger assembly and a means for the user to manipulate the device during use by grasping a handle member that will circumvent the need for the user to grasp the lubricated shaft. The handle member also serves as a stop to prevent full insertion into the orifice during usage.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
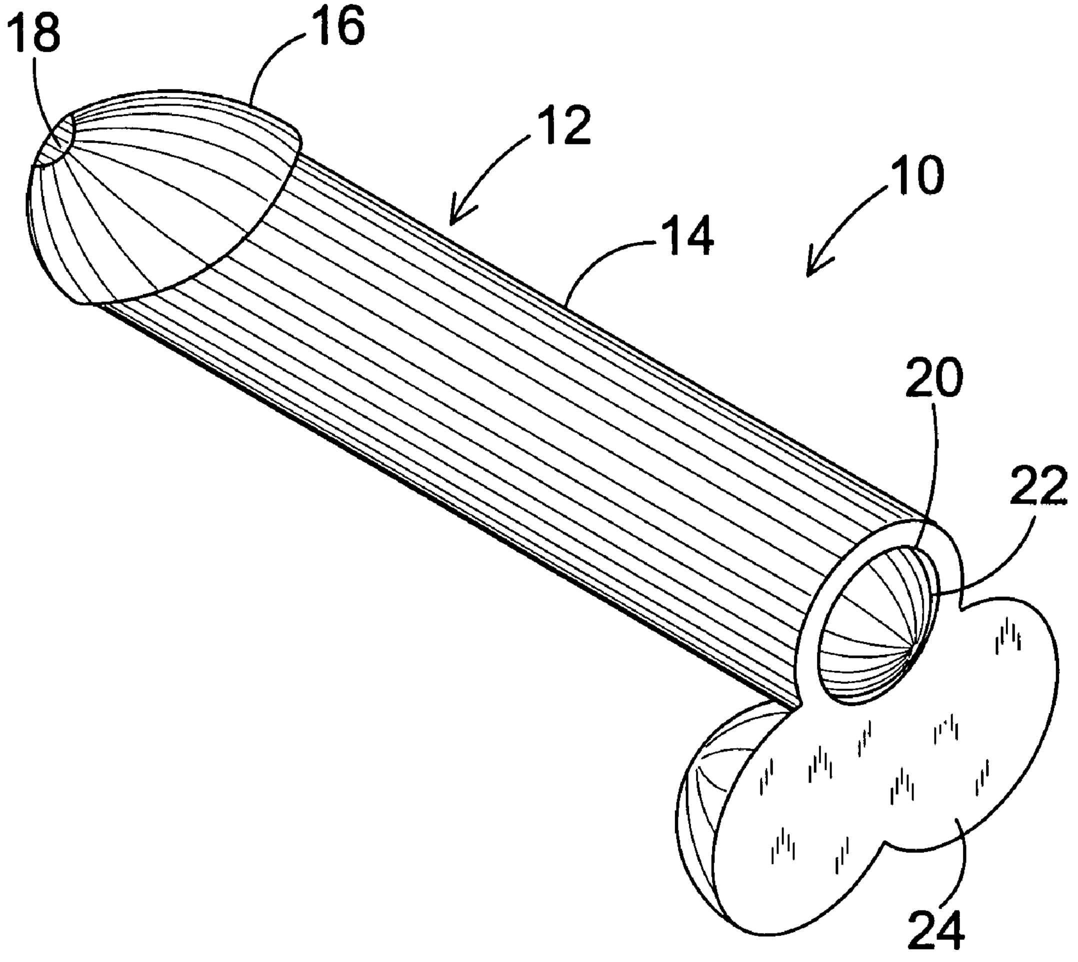
FIG. 1 is a perspective view of the lubricating sexual aid of the present invention.

Turning now descriptively to the drawings, in which similar reference characters denote similar elements throughout the several views, the Figures illustrate the lubricating sexual aid of the present invention. With regard to the reference numerals used, the following numbering is used throughout the various drawing figures.

10 lubricating sexual aid of the present invention
12 body
14 shaft
16 head
18 egress aperture
20 bore
22 pressure plunger
24 handle
26 one-way value
27 roller
28 piston
30 lubrication reservoir
32 air reservoir
36 lubricant
38 threads
40 syringe plunger
42 plunger cap

DETAILED DESCRIPTION OF THE PREFERRED EMBODIMENT

The following discussion describes in detail one embodiment of the invention and several variations of that embodiment. This discussion should not be construed, however, as limiting the invention to those particular embodiments, practitioners skilled in the art will recognize numerous other embodiments as well. For definition of the complete scope of the invention, the reader is directed to appended claims.

Turning now descriptively to the drawings, in which similar reference characters denote similar elements throughout the several views, FIGS. 1 through 10 illustrate a lubricating sexual aid of the present invention which is indicated generally by the numeral 10.

Figure 2:
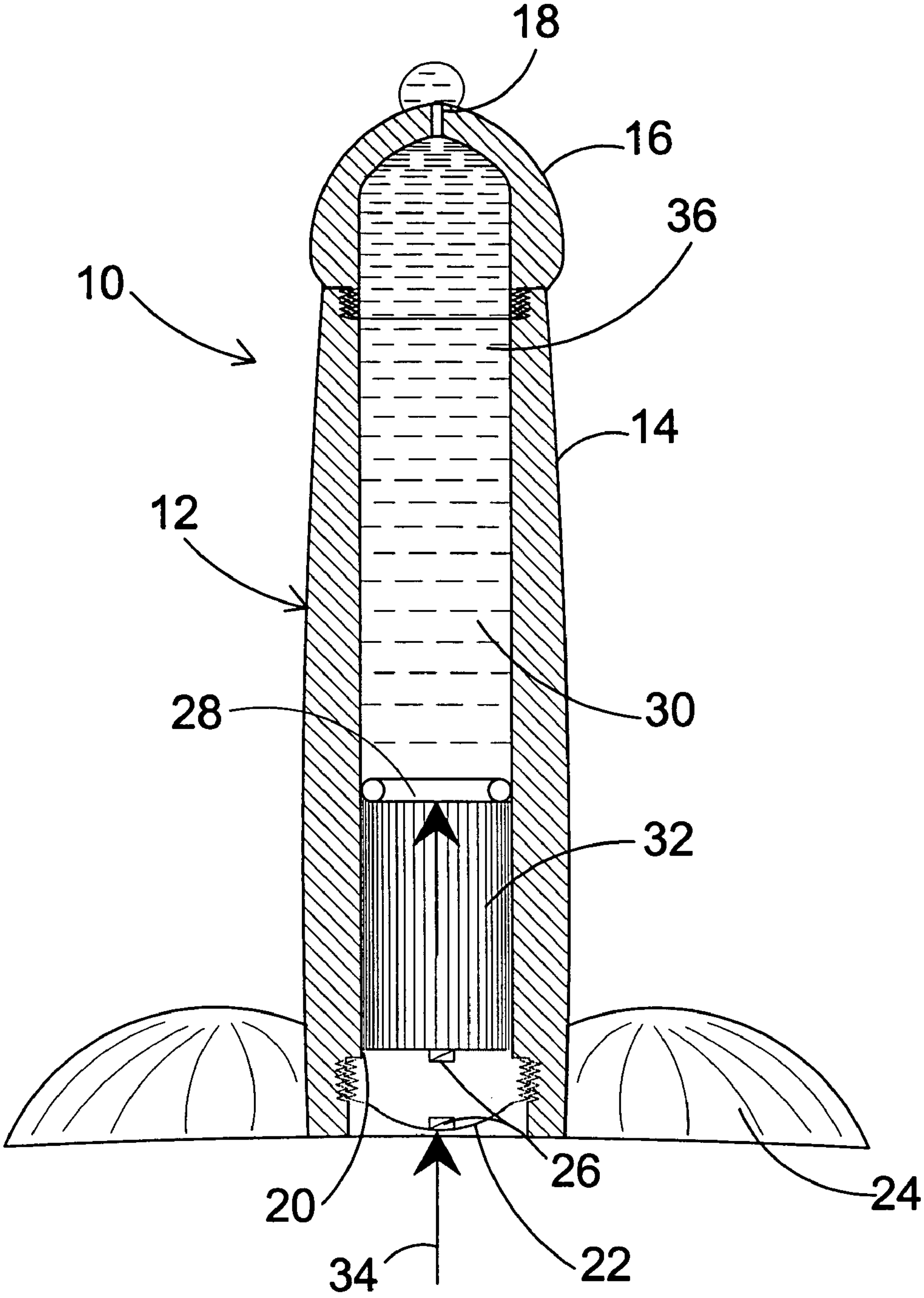
FIG. 2 is a sectional view of the lubricating sexual aid of the present invention.
Figure 3:
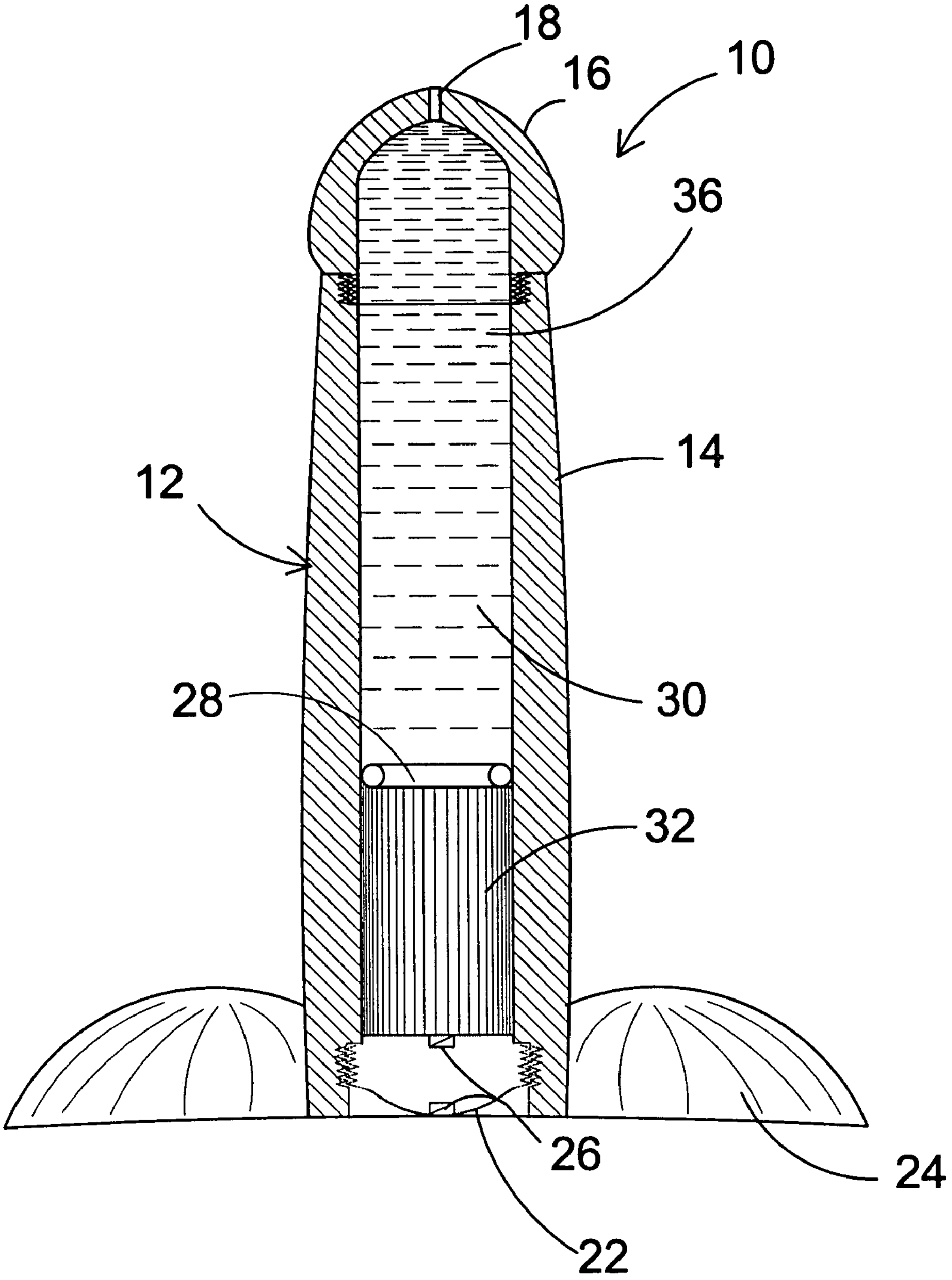
FIG. 3 is a sectional view of the lubricating sexual aid of the present invention.
Figure 4:
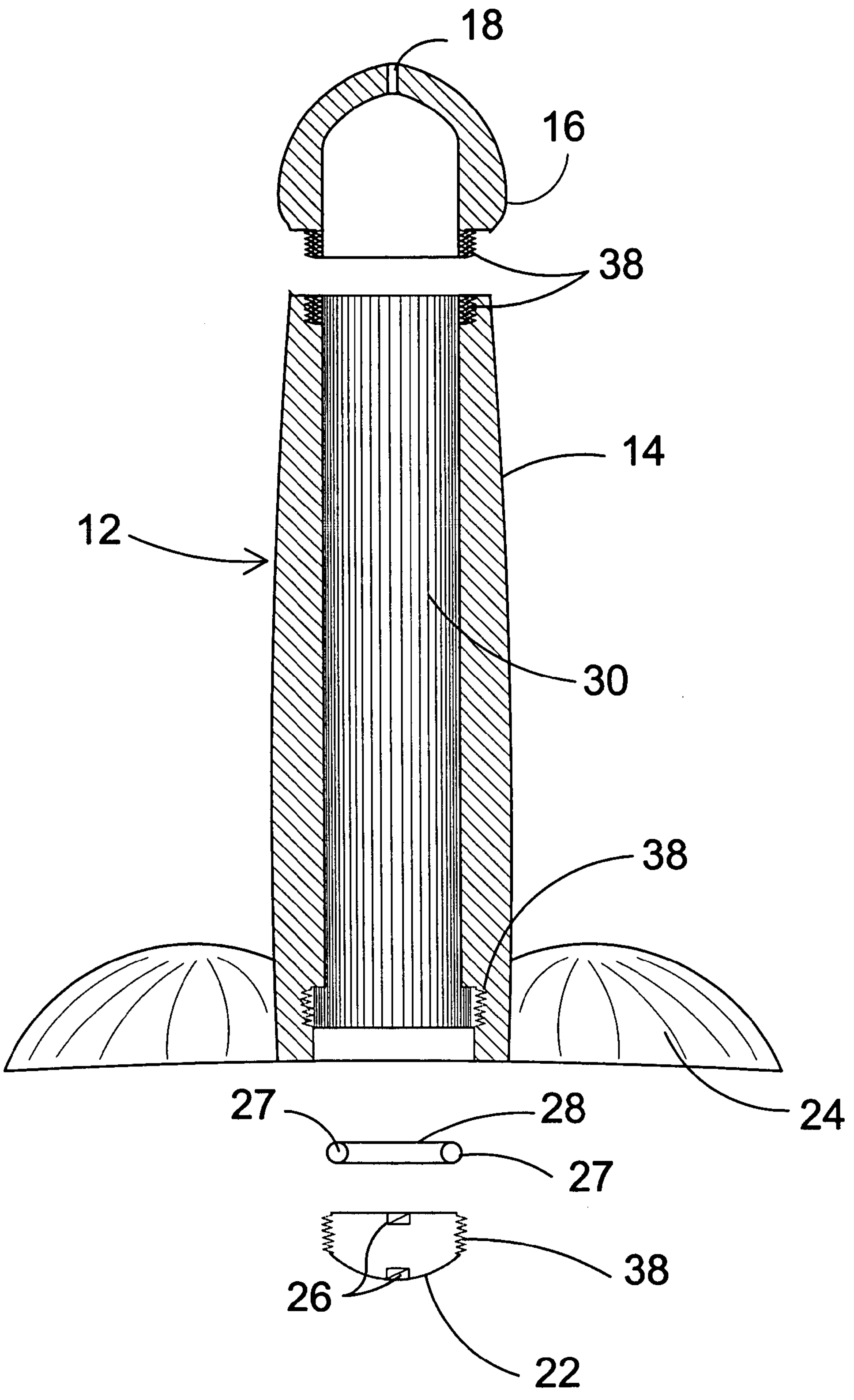
FIG. 4 is an exploded view of the lubricating sexual aid of the present invention.

FIG. 1 is a perspective view of the lubricating sexual aid 10 of the present invention. The lubricating sexual aid 10 is preferably formed in the shape of a penis. The aid 10 includes a body 12 having a handle 24 positioned at a base end thereof. The body 12 includes a shaft 14 and a head 16. The shaft 14 includes a bore 20 extending along the entire length of thereof. The head 16 is positioned at a distal end of the shaft 14 opposite the handle 24. The head 16 is substantially hemispherical in shape and includes an egress aperture 18 positioned at an apex thereof. As shown in FIGS. 2–4, the bore 20 extending through the shaft 14 forms a reservoir 30 for receiving a lubricant 36 therein. The lubricant is preferably K-Y JELLY™. However, any lubricant that is approved for safe use and that will not irritate or harm a human being may be used with the sexual aid 10 if the present invention. Upon the lubricant being received within the reservoir 30, a plunger 22 is received within the bore 20. When the plunger 22 is depressed, the lubricant 36 is forced out from the reservoir 30 through the egress aperture 18.

The sexual aid 10 of the present invention is selectively insertable into an orifice of the human body such as the vagina or anus in order to stimulate sexual pleasure of the user. It is desirable to apply a lubricant to a sexual aid in order to minimize irritation therby increasing the level of pleasure provided by the sexual aid. Thus, the lubricating sexual aid 10 of the present invention allows for a user to deposit the lubricant 326 within the orifice while the aid 10 is being used. Upon insertion of the lubricating sexual aid 10, the user depresses the plunger 22 which causes the lubricant 36 to exit through the egress aperture 18 of the head 16. The lubricant 36 contacts the walls of the orifice and is caused to be spread about an exterior surface of the head 16 and shaft 14 of the body 12 thereby reducing and/or eliminating any friction typically associated with repeated removal and insertion of the aid 10.

By using the lubricating sexual aid 10 of the present invention the user is able to avoid getting lubricant on the users hands and making a greasy mess. The present invention seeks to overcome the shortcoming of the prior art by introducing a lubricating sexual aid that virtually eliminates hand contact with the lubricant.

FIG. 2 is a sectional view of the lubricating sexual aid of the present invention. The lubricating sexual aid 10 is preferably formed in the shape of a penis. The aid 10 includes the body 12 having the handle 24 positioned at a base end thereof. The body 12 includes the shaft 14 and the head 16. The shaft 14 includes the bore 20 extending along the entire length of thereof. The head 16 is positioned at the distal end of the shaft 14 opposite the handle 24. The head 16 is substantially hemispherical in shape and includes the egress aperture 18 positioned at an apex thereof. The bore 20 extending through the shaft 14 forms the reservoir 30 for receiving the lubricant 36 therein. The lubricant is preferably K-Y JELLY™. However, any lubricant that is approved for safe use and that will not irritate or harm a human may be used with the sexual aid 10 if the present invention.

Upon the lubricant being received within the reservoir 30, a piston 28 having a plurality of rollers 27 is inserted into the bore 20 and is selectively moveable along the length thereof. The plunger 22 is received within the bore 20. The plunger includes one way values 26. Depressing the plunger 22 causes the exterior one way valve 26 to close with the enclosed air forced through the interior one way valve 26 pressurizing the reservoir causing the piston 28 to move forward The pressure caused by the air escaping causes the rollers 27 to roll along an inner surface of the reservoir and the piston forces lubricant 36 out through the egress aperture of the head 16. When the plunger 22 is depressed in a direction illustrated by the arrow labeled with the reference numeral 34, the lubricant 36 is forced out from the reservoir 30 through the egress aperture 18. The plunger 22 retracts when the reservoir 32 is refilled thus returning it to full status.

The sexual aid 10 of the present invention is selectively insertable into an orifice of the human body such as the vagina or anus in order to stimulate sexual pleasure of the user. The user is able to hold and manipulate the aid 10 by the handle 24 which is formed in a shape substantially similar to a pair of testicles. This is shown for exemplary purpose only and the handle 24 may be formed in any shape that is comfortable for the user to grip and use the aid 10 of the present invention. It is desirable to apply a lubricant to a sexual aid in order to minimize irritation therby increasing the level of pleasure provided by the sexual aid. Thus, the lubricating sexual aid 10 of the present invention allows for a user to deposit the lubricant 326 within the orifice while the aid 10 is being used. Upon insertion of the lubricating sexual aid 10, the user depresses the plunger 22 which causes the lubricant 36 to exit through the egress aperture 18 of the head 16. The lubricant 36 contacts the walls of the orifice and is caused to be spread about an exterior surface of the head 16 and shaft 14 of the body 12 thereby reducing and/or eliminating any friction typically associated with repeated removal and insertion of the aid 10.

Shown in FIG. 2 is the lubricating sexual aid 10 of the present invention having the reserivoir 30 filled with lubricant 36 and is ready for use.

FIG. 3 is a sectional view of the lubricating sexual aid of the present invention. The lubricating sexual aid 10 is preferably formed in the shape of a penis. The aid 10 includes the body 12 having the handle 24 positioned at a base end thereof. The body 12 includes the shaft 14 and the head 16. The shaft 14 includes the bore 20 extending along the entire length of thereof. The head 16 is positioned at the distal end of the shaft 14 opposite the handle 24. The head 16 is substantially hemispherical in shape and includes the egress aperture 18 positioned at an apex thereof. The bore 20 extending through the shaft 14 forms the reservoir 30 for receiving the lubricant 36 therein. The lubricant is preferably K-Y JELLY™. However, any lubricant that is approved for safe use and that will not irritate or harm a human may be used with the sexual aid 10 if the present invention.

Upon the lubricant being received within the reservoir 30, the piston 28 having the plurality of rollers 27 is inserted into the bore 20 and is selectively moveable along the length thereof. The plunger 22 is received within the bore 20. The plunger includes one way values 26. Depressing the plunger 22 causes the exterior one way valve 26 to close with the enclosed air forced through the interior one way valve 26 pressurizing the reservoir causing the piston 28 to move forward The pressure caused by the air escaping causes the rollers 27 to roll along an inner surface of the reservoir and the piston forces lubricant 36 out through the egress aperture of the head 16. When the plunger 22 is depressed in a direction illustrated by the arrow labeled with the reference numeral 34, the lubricant 36 is forced out from the reservoir 30 through the egress aperture 18. The plunger 22 retracts when the reservoir 32 is refilled thus returning it to full status.

The sexual aid 10 of the present invention is selectively insertable into an orifice of the human body such as the vagina or anus in order to stimulate sexual pleasure of the user. The user is able to hold and manipulate the aid 10 by the handle 24 which is formed in a shape substantially similar to a pair of testicles. This is shown for exemplary purpose only and the handle 24 may be formed in any shape that is comfortable for the user to grip and use the aid 10 of the present invention. It is desirable to apply a lubricant to a sexual aid in order to minimize irritation therby increasing the level of pleasure provided by the sexual aid. Thus, the lubricating sexual aid 10 of the present invention allows for a user to deposit the lubricant 326 within the orifice while the aid 10 is being used. Upon insertion of the lubricating sexual aid 10, the user depresses the plunger 22 which causes the lubricant 36 to exit through the egress aperture 18 of the head 16. The lubricant 36 contacts the walls of the orifice and is caused to be spread about an exterior surface of the head 16 and shaft 14 of the body 12 thereby reducing and/or eliminating any friction typically associated with repeated removal and insertion of the aid 10.

FIG. 4 is an exploded view of the lubricating sexual aid of the present invention. The lubricating sexual aid 10 is preferably formed in the shape of a penis. The aid 10 includes the body 12 having the handle 24 positioned at a base end thereof. The body 12 includes the shaft 14 and the head 16. The shaft 14 includes the bore 20 extending along the entire length of thereof. The head 16 is positioned at the distal end of the shaft 14 opposite the handle 24. The head 16 is substantially hemispherical in shape and includes the egress aperture 18 positioned at an apex thereof. The bore 20 extending through the shaft 14 forms the reservoir 30 for receiving the lubricant 36 therein. The lubricant is preferably K-Y JELLY™. However, any lubricant that is approved for safe use and that will not irritate or harm a human may be used with the sexual aid 10 if the present invention.

Upon the lubricant being received within the reservoir 30, the piston 28 having the plurality of rollers 27 is inserted into the bore 20 and is selectively moveable along the length thereof. The plunger 22 is received within the bore 20. The plunger includes one way values 26. Depressing the plunger 22 causes the exterior one way valve 26 to close with the enclosed air forced through the interior one way valve 26 pressurizing the reservoir causing the piston 28 to move forward The pressure caused by the air escaping causes the rollers 27 to roll along an inner surface of the reservoir and the piston forces lubricant 36 out through the egress aperture of the head 16. When the plunger 22 is depressed in a direction illustrated by the arrow labeled with the reference numeral 34, the lubricant 36 is forced out from the reservoir 30 through the egress aperture 18. The plunger 22 retracts when the reservoir 32 is refilled thus returning it to full status.

The sexual aid 10 of the present invention is selectively insertable into an orifice of the human body such as the vagina or anus in order to stimulate sexual pleasure of the user. The user is able to hold and manipulate the aid 10 by the handle 24 which is formed in a shape substantially similar to a pair of testicles. This is shown for exemplary purpose only and the handle 24 may be formed in any shape that is comfortable for the user to grip and use the aid 10 of the present invention. It is desirable to apply a lubricant to a sexual aid in order to minimize irritation therby increasing the level of pleasure provided by the sexual aid. Thus, the lubricating sexual aid 10 of the present invention allows for a user to deposit the lubricant 326 within the orifice while the aid 10 is being used. Upon insertion of the lubricating sexual aid 10, the user depresses the plunger 22 which causes the lubricant 36 to exit through the egress aperture 18 of the head 16. The lubricant 36 contacts the walls of the orifice and is caused to be spread about an exterior surface of the head 16 and shaft 14 of the body 12 thereby reducing and/or eliminating any friction typically associated with repeated removal and insertion of the aid 10.

Shown is an exploded view of the present invention disassembled for cleaning and refilling thereof. The head 16 is removeably connected to the shaft 14 via threads 38 whereby upon rotating the head 16 the threads 38 matchup and the head may be screwed on to the shaft 14. The piston 28 can also be removed for cleaning thereof. The plunger 22 is screwably connected to the base of the shaft 14 via a second set of threads 38. When the desired amount of lubricant 36 has been added to the reservoir 30, the head 16 is attached to the shaft 14. The piston 28 is inserted through the bore 20 and the plunger is then screwed on to the base of the shaft 14 thereby placing the lubricating sexual aid in position for use.

Figure 5:
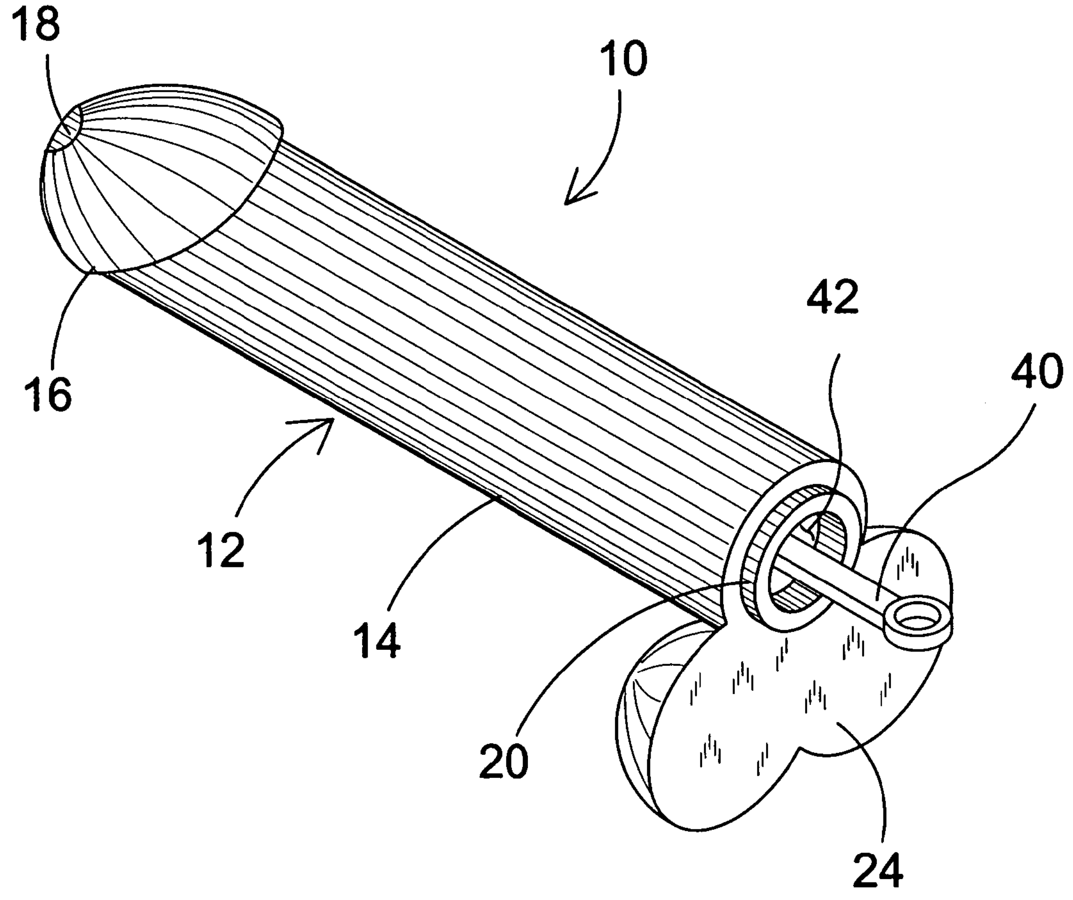
FIG. 5 is a perspective view of an alternate embodiment of the lubricating sexual aid of the present invention.

FIG. 5 is a perspective view of an alternate embodiment of the lubricating sexual aid of the present invention. The lubricating sexual aid 10 is preferably formed in the shape of a penis. The aid 10 includes a body 12 having a handle 24 positioned at a base end thereof. The body 12 includes a shaft 14 and a head 16. The shaft 14 includes a bore 20 extending along the entire length of thereof. The head 16 is positioned at a distal end of the shaft 14 opposite the handle 24. The head 16 is substantially hemispherical in shape and includes an egress aperture 18 positioned at an apex thereof. As shown in FIGS. 6–10, the bore 20 extending through the shaft 14 forms a reservoir 30 for receiving a lubricant 36 therein. The lubricant is preferably K-Y JELLY™. However, any lubricant that is approved for safe use and that will not irritate or harm a human being may be used with the sexual aid 10 if the present invention. Upon the lubricant being received within the reservoir 30, a plunger 40 is received within the bore 20. A plunger cap 42 secures the plunger 40 within the bore 20. The plunger 40 further includes a ring 41 for receiving at least one of a finger and a thumb therethrough. Upon the ring 41 receiving the at least one of the finger and thumb, the plunger 40 is move along the interior of the bore 20 thereby causing the lubricant 36 to be forced out from the reservoir 30 through the egress aperture 18.

The sexual aid 10 of the present invention is selectively insertable into an orifice of the human body such as the vagina or anus in order to stimulate sexual pleasure of the user. It is desirable to apply a lubricant to a sexual aid in order to minimize irritation therby increasing the level of pleasure provided by the sexual aid. Thus, the lubricating sexual aid 10 of the present invention allows for a user to deposit the lubricant 326 within the orifice while the aid 10 is being used. Upon insertion of the lubricating sexual aid 10, the user depresses the plunger 22 which causes the lubricant 36 to exit through the egress aperture 18 of the head 16. The lubricant 36 contacts the walls of the orifice and is caused to be spread about an exterior surface of the head 16 and shaft 14 of the body 12 thereby reducing and/or eliminating any friction typically associated with repeated removal and insertion of the aid 10.

The plunger 40 as shown in FIG. 5 differs from the plunger 22 shown and described above in FIGS. 1–4. Specifically, the plunger 40 is substantially similar to a syringe plunger and requires pressure to be applied in a first direction to force the lubricant out from the reservoir 30 through the egress aperture 18. While two varying plungers 22, 40 are shown throughout FIGS. 1–10, any suitable plunger means may be adapted to the present invention although the preferred embodiment is one which would provide a flat base thereby enabling the user to stand the sexual aid 10 on the base and avoid having the shaft 14 contaminated by contacting a surface.

Figure 6:
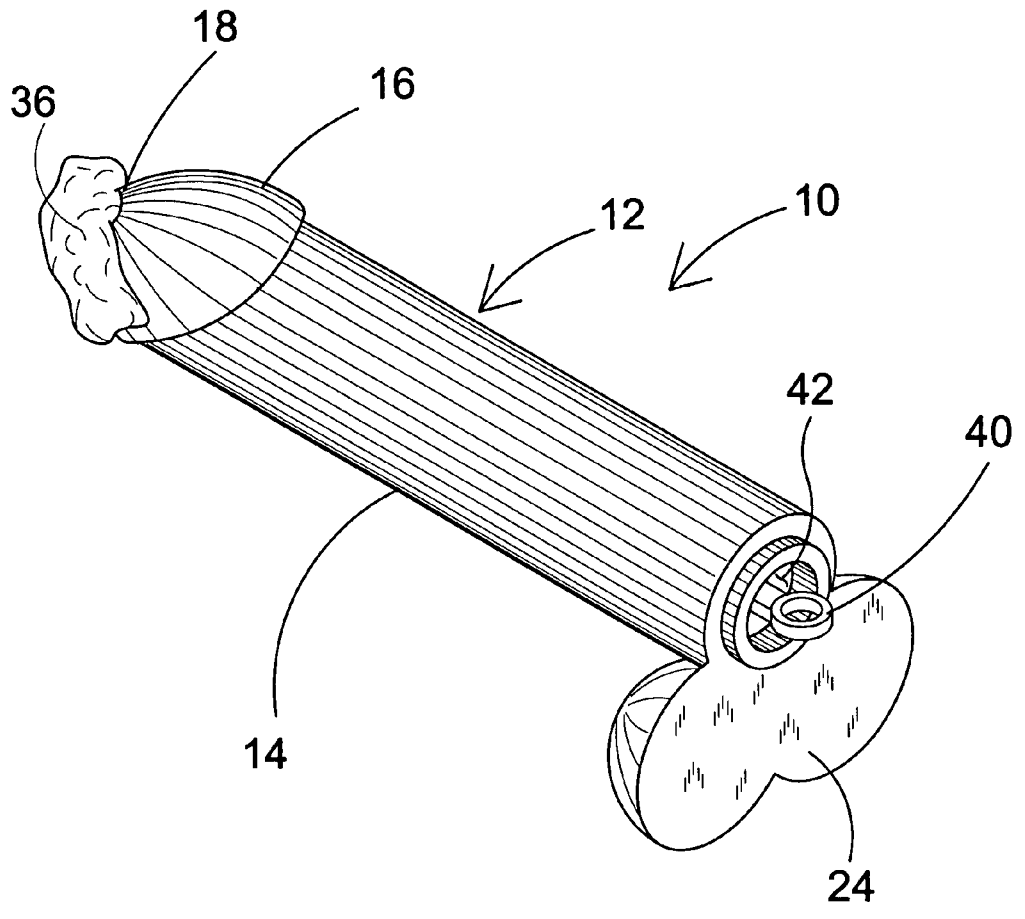
FIG. 6 is a perspective view of the lubricating sexual aid of the present invention in use.

FIG. 6 is a perspective view of the lubricating sexual aid of the present invention in use. The lubricating sexual aid 10 is preferably formed in the shape of a penis. The aid 10 includes a body 12 having a handle 24 positioned at a base end thereof. The body 12 includes a shaft 14 and a head 16. The shaft 14 includes a bore 20 extending along the entire length of thereof. The head 16 is positioned at a distal end of the shaft 14 opposite the handle 24. The head 16 is substantially hemispherical in shape and includes an egress aperture 18 positioned at an apex thereof. As shown in FIGS. 6–10, the bore 20 extending through the shaft 14 forms a reservoir 30 for receiving a lubricant 36 therein. The lubricant is preferably K-Y JELLY™. However, any lubricant that is approved for safe use and that will not irritate or harm a human being may be used with the sexual aid 10 if the present invention. Upon the lubricant being received within the reservoir 30, a plunger 40 is received within the bore 20. A plunger cap 42 secures the plunger 40 within the bore 20. The plunger 40 further includes a ring 41 for receiving at least one of a finger and a thumb therethrough. Upon the ring 41 receiving the at least one of the finger and thumb, the plunger 40 is move along the interior of the bore 20 thereby causing the lubricant 36 to be forced out from the reservoir 30 through the egress aperture 18.

The sexual aid 10 of the present invention is selectively insertable into an orifice of the human body such as the vagina or anus in order to stimulate sexual pleasure of the user. It is desirable to apply a lubricant to a sexual aid in order to minimize irritation therby increasing the level of pleasure provided by the sexual aid. Thus, the lubricating sexual aid 10 of the present invention allows for a user to deposit the lubricant 326 within the orifice while the aid 10 is being used. Upon insertion of the lubricating sexual aid 10, the user depresses the plunger 22 which causes the lubricant 36 to exit through the egress aperture 18 of the head 16. The lubricant 36 contacts the walls of the orifice and is caused to be spread about an exterior surface of the head 16 and shaft 14 of the body 12 thereby reducing and/or eliminating any friction typically associated with repeated removal and insertion of the aid 10.

Shown is the present invention wherein the plunger 40 has been depressed thereby pressurizing the quantity of lubricant 36 contained within the reservoir 30 as shown hereinafter with specific reference to FIGS. 7–10 and forcing the lubricant 36 through the egress aperture 18.

Figure 7:
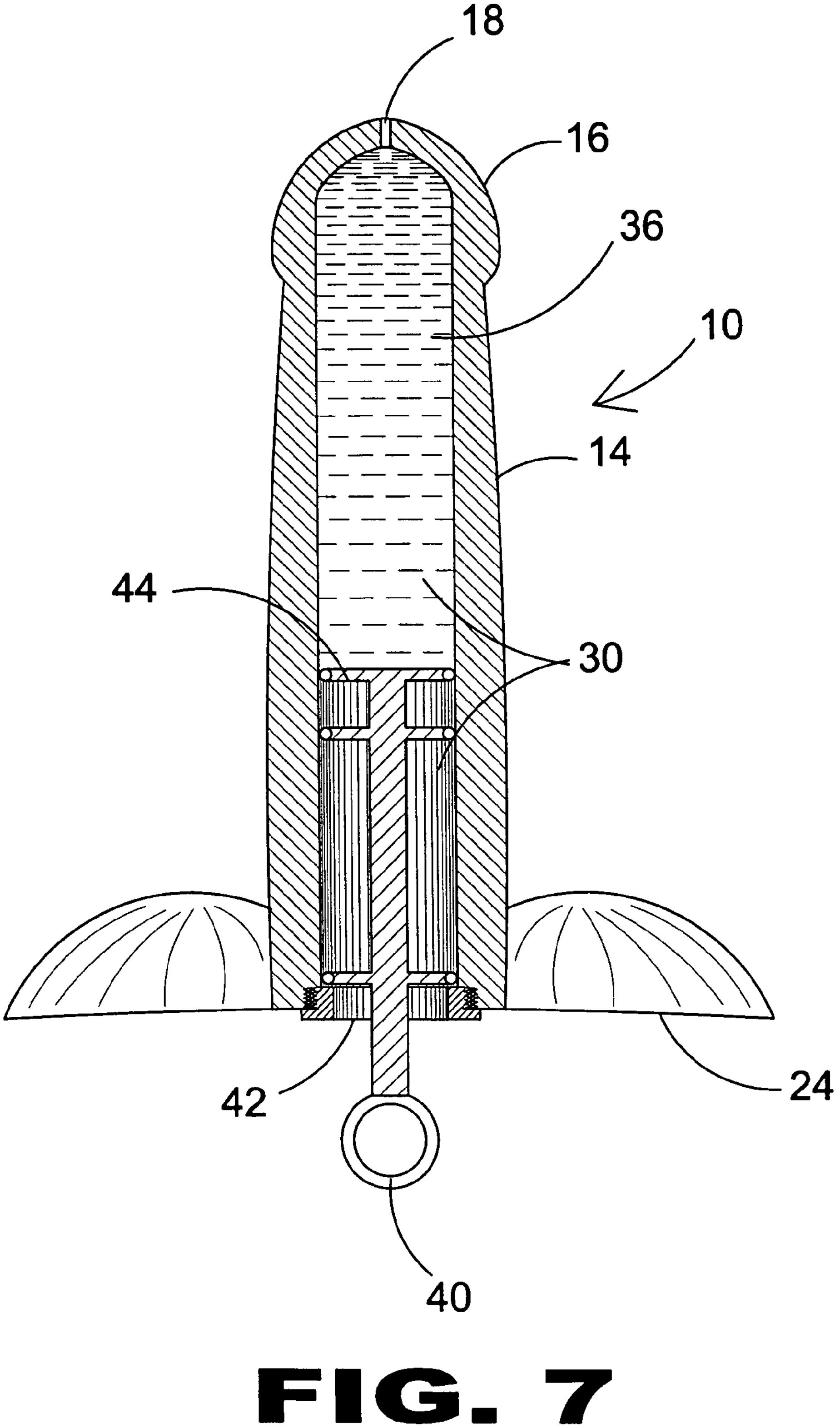
FIG. 7 is a sectional view of the alternate embodiment of the lubricating sexual aid of the present invention.

FIG. 7 is a sectional view of the alternate embodiment of the lubricating sexual aid of the present invention. The lubricating sexual aid 10 is preferably formed in the shape of a penis. The aid 10 includes the body 12 having the handle 24 positioned at a base end thereof. The body 12 includes the shaft 14 and the head 16. The shaft 14 includes the bore 20 extending along the entire length of thereof. The head 16 is positioned at the distal end of the shaft 14 opposite the handle 24. The head 16 is substantially hemispherical in shape and includes the egress aperture 18 positioned at an apex thereof. The bore 20 extending through the shaft 14 forms the reservoir 30 for receiving the lubricant 36 therein. The lubricant is preferably K-Y JELLY™. However, any lubricant that is approved for safe use and that will not irritate or harm a human may be used with the sexual aid 10 if the present invention.

Upon the lubricant being received within the reservoir 30, a plunger 40 is received within the bore 20. A plunger cap 42 secures the plunger 40 within the bore 20. The plunger 40 includes a flat head 44 for applying a pressure to the lubricant 36 contained in the reservoir 30. The plunger further includes the ring 41 for receiving at least one of a finger and a thumb therethrough. Upon the ring 41 receiving the at least one of the finger and thumb, the plunger 40 is move along the interior of the bore 20 and the flat head 44 applies pressure to the lubricant 36 thereby forcing the lubricant 36 out from the reservoir 30 through the egress aperture 18. When the plunger 40 is depressed in a direction illustrated by the arrow labeled with the reference numeral 34, the lubricant 36 is forced out from the reservoir 30 through the egress aperture 18. The plunger 40 retracts when the reservoir 32 is refilled thus returning it to full status.

The sexual aid 10 of the present invention is selectively insertable into an orifice of the human body such as the vagina or anus in order to stimulate sexual pleasure of the user. The user is able to hold and manipulate the aid 10 by the handle 24 which is formed in a shape substantially similar to a pair of testicles. This is shown for exemplary purpose only and the handle 24 may be formed in any shape that is comfortable for the user to grip and use the aid 10 of the present invention. It is desirable to apply a lubricant to a sexual aid in order to minimize irritation therby increasing the level of pleasure provided by the sexual aid. Thus, the lubricating sexual aid 10 of the present invention allows for a user to deposit the lubricant 36 within the orifice while the aid 10 is being used. Upon insertion of the lubricating sexual aid 10, the user depresses the plunger 40 which causes the lubricant 36 to exit through the egress aperture 18 of the head 16. The lubricant 36 contacts the walls of the orifice and is caused to be spread about an exterior surface of the head 16 and shaft 14 of the body 12 thereby reducing and/or eliminating any friction typically associated with repeated removal and insertion of the aid 10.

Figure 8:
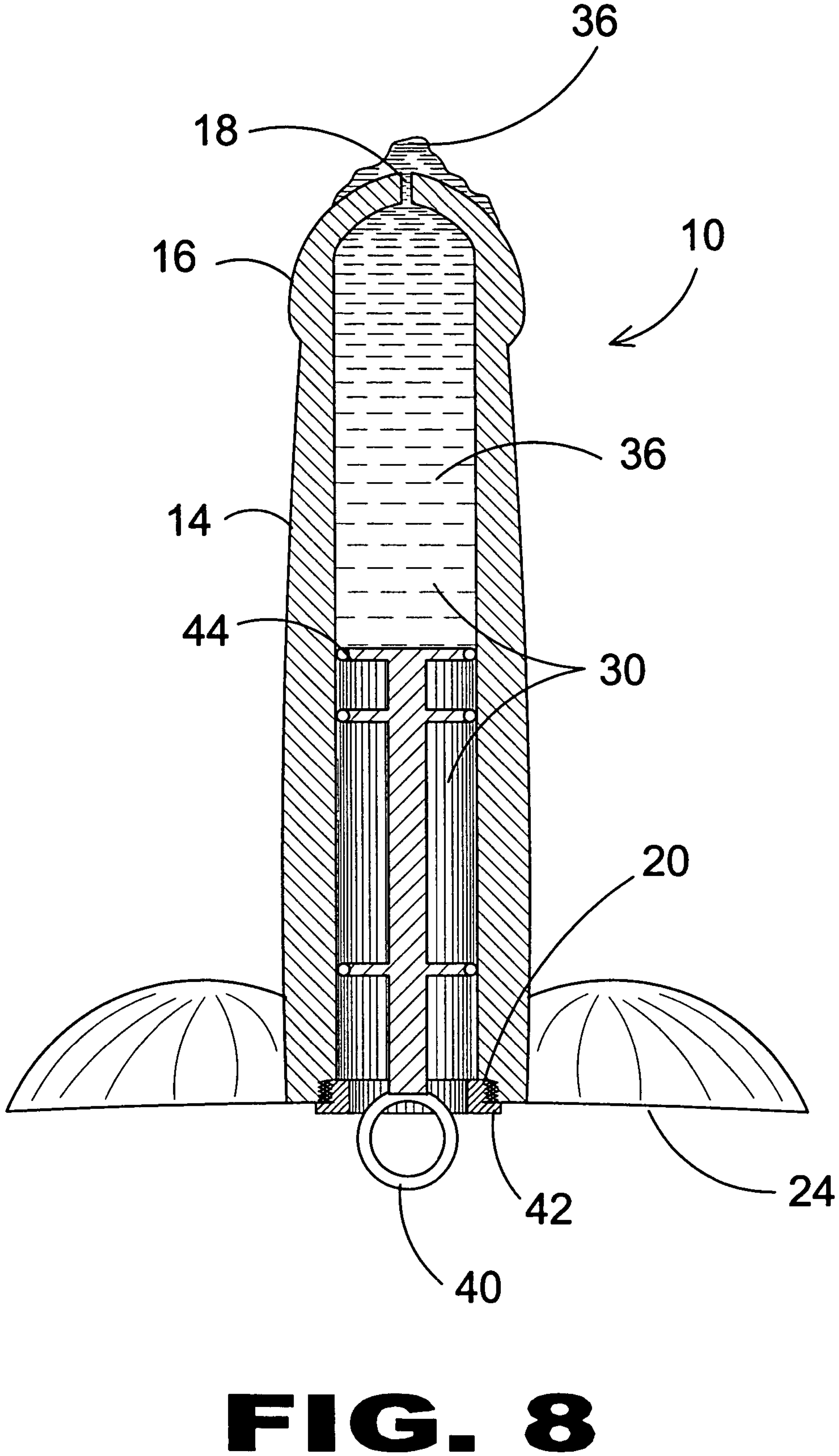
FIG. 8 is a sectional view of the alternate embodiment of the lubricating sexual aid of the present invention.

FIG. 8 is a sectional view of the alternate embodiment of the lubricating sexual aid of the present invention. The lubricating sexual aid 10 is preferably formed in the shape of a penis. The aid 10 includes the body 12 having the handle 24 positioned at a base end thereof. The body 12 includes the shaft 14 and the head 16. The shaft 14 includes the bore 20 extending along the entire length of thereof. The head 16 is positioned at the distal end of the shaft 14 opposite the handle 24. The head 16 is substantially hemispherical in shape and includes the egress aperture 18 positioned at an apex thereof. The bore 20 extending through the shaft 14 forms the reservoir 30 for receiving the lubricant 36 therein. The lubricant is preferably K-Y JELLY™. However, any lubricant that is approved for safe use and that will not irritate or harm a human may be used with the sexual aid 10 if the present invention.

Upon the lubricant being received within the reservoir 30, a plunger 40 is received within the bore 20. A plunger cap 42 secures the plunger 40 within the bore 20. The plunger 40 includes a flat head 44 for applying a pressure to the lubricant 36 contained in the reservoir 30. The plunger further includes the ring 41 for receiving at least one of a finger and a thumb therethrough. Upon the ring 41 receiving the at least one of the finger and thumb, the plunger 40 is move along the interior of the bore 20 and the flat head 44 applies pressure to the lubricant 36 thereby forcing the lubricant 36 out from the reservoir 30 through the egress aperture 18. When the plunger 40 is depressed in a direction illustrated by the arrow labeled with the reference numeral 34, the lubricant 36 is forced out from the reservoir 30 through the egress aperture 18. The plunger 40 retracts when the reservoir 32 is refilled thus returning it to full status.

The sexual aid 10 of the present invention is selectively insertable into an orifice of the human body such as the vagina or anus in order to stimulate sexual pleasure of the user. The user is able to hold and manipulate the aid 10 by the handle 24 which is formed in a shape substantially similar to a pair of testicles. This is shown for exemplary purpose only and the handle 24 may be formed in any shape that is comfortable for the user to grip and use the aid 10 of the present invention. It is desirable to apply a lubricant to a sexual aid in order to minimize irritation therby increasing the level of pleasure provided by the sexual aid. Thus, the lubricating sexual aid 10 of the present invention allows for a user to deposit the lubricant 36 within the orifice while the aid 10 is being used. Upon insertion of the lubricating sexual aid 10, the user depresses the plunger 40 which causes the lubricant 36 to exit through the egress aperture 18 of the head 16. The lubricant 36 contacts the walls of the orifice and is caused to be spread about an exterior surface of the head 16 and shaft 14 of the body 12 thereby reducing and/or eliminating any friction typically associated with repeated removal and insertion of the aid 10.

Shown is the present invention wherein the plunger 40 has been depressed thereby pressurizing the quantity of lubricating gel 36 contained within the reservoir 30 and forcing it through the egress aperture 18 onto the exterior surface where it will spread as the sexual aid 10 of the present invention is inserted into the orifice.

Figure 9:
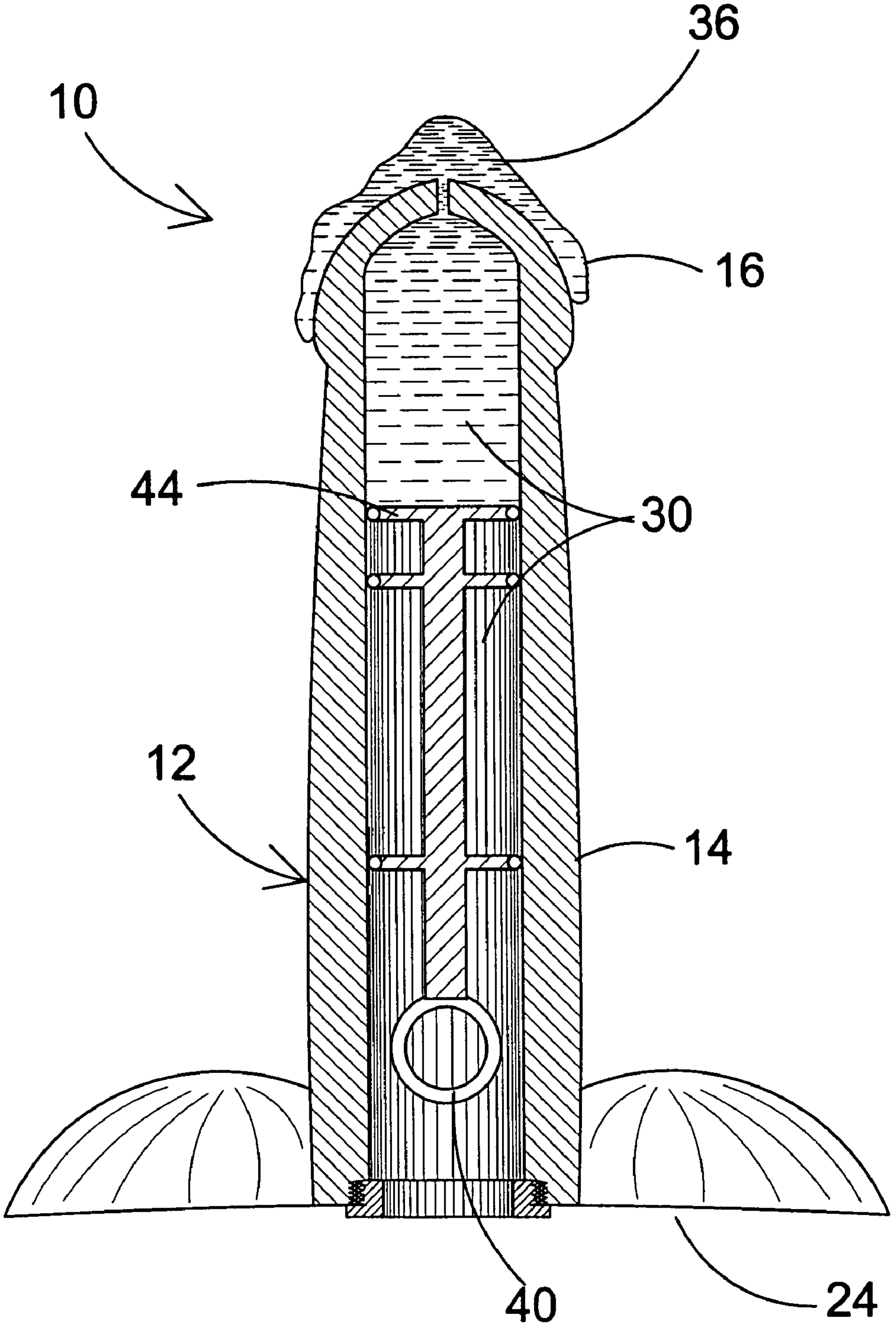
FIG. 9 is a sectional view of the alternate embodiment of the lubricating sexual aid of the present invention.

FIG. 9 is a sectional view of the alternate embodiment of the lubricating sexual aid of the present invention. The lubricating sexual aid 10 is preferably formed in the shape of a penis. The aid 10 includes the body 12 having the handle 24 positioned at a base end thereof. The body 12 includes the shaft 14 and the head 16. The shaft 14 includes the bore 20 extending along the entire length of thereof. The head 16 is positioned at the distal end of the shaft 14 opposite the handle 24. The head 16 is substantially hemispherical in shape and includes the egress aperture 18 positioned at an apex thereof. The bore 20 extending through the shaft 14 forms the reservoir 30 for receiving the lubricant 36 therein. The lubricant is preferably K-Y JELLY™. However, any lubricant that is approved for safe use and that will not irritate or harm a human may be used with the sexual aid 10 if the present invention.

Upon the lubricant being received within the reservoir 30, a plunger 40 is received within the bore 20. A plunger cap 42 secures the plunger 40 within the bore 20. The plunger 40 includes a flat head 44 for applying a pressure to the lubricant 36 contained in the reservoir 30. The plunger further includes the ring 41 for receiving at least one of a finger and a thumb therethrough. Upon the ring 41 receiving the at least one of the finger and thumb, the plunger 40 is move along the interior of the bore 20 and the flat head 44 applies pressure to the lubricant 36 thereby forcing the lubricant 36 out from the reservoir 30 through the egress aperture 18. When the plunger 40 is depressed in a direction illustrated by the arrow labeled with the reference numeral 34, the lubricant 36 is forced out from the reservoir 30 through the egress aperture 18. The plunger 40 retracts when the reservoir 32 is refilled thus returning it to full status.

The sexual aid 10 of the present invention is selectively insertable into an orifice of the human body such as the vagina or anus in order to stimulate sexual pleasure of the user. The user is able to hold and manipulate the aid 10 by the handle 24 which is formed in a shape substantially similar to a pair of testicles. This is shown for exemplary purpose only and the handle 24 may be formed in any shape that is comfortable for the user to grip and use the aid 10 of the present invention. It is desirable to apply a lubricant to a sexual aid in order to minimize irritation therby increasing the level of pleasure provided by the sexual aid. Thus, the lubricating sexual aid 10 of the present invention allows for a user to deposit the lubricant 36 within the orifice while the aid 10 is being used. Upon insertion of the lubricating sexual aid 10, the user depresses the plunger 40 which causes the lubricant 36 to exit through the egress aperture 18 of the head 16. The lubricant 36 contacts the walls of the orifice and is caused to be spread about an exterior surface of the head 16 and shaft 14 of the body 12 thereby reducing and/or eliminating any friction typically associated with repeated removal and insertion of the aid 10.

The user determines when and how much lubricant 36 is distributed to the outer surface of the device by simply depressing the plunger 40 as needed. The simplicity of the design assures effectiveness, longevity of components and low cost in manufacturing.

Figure 10:
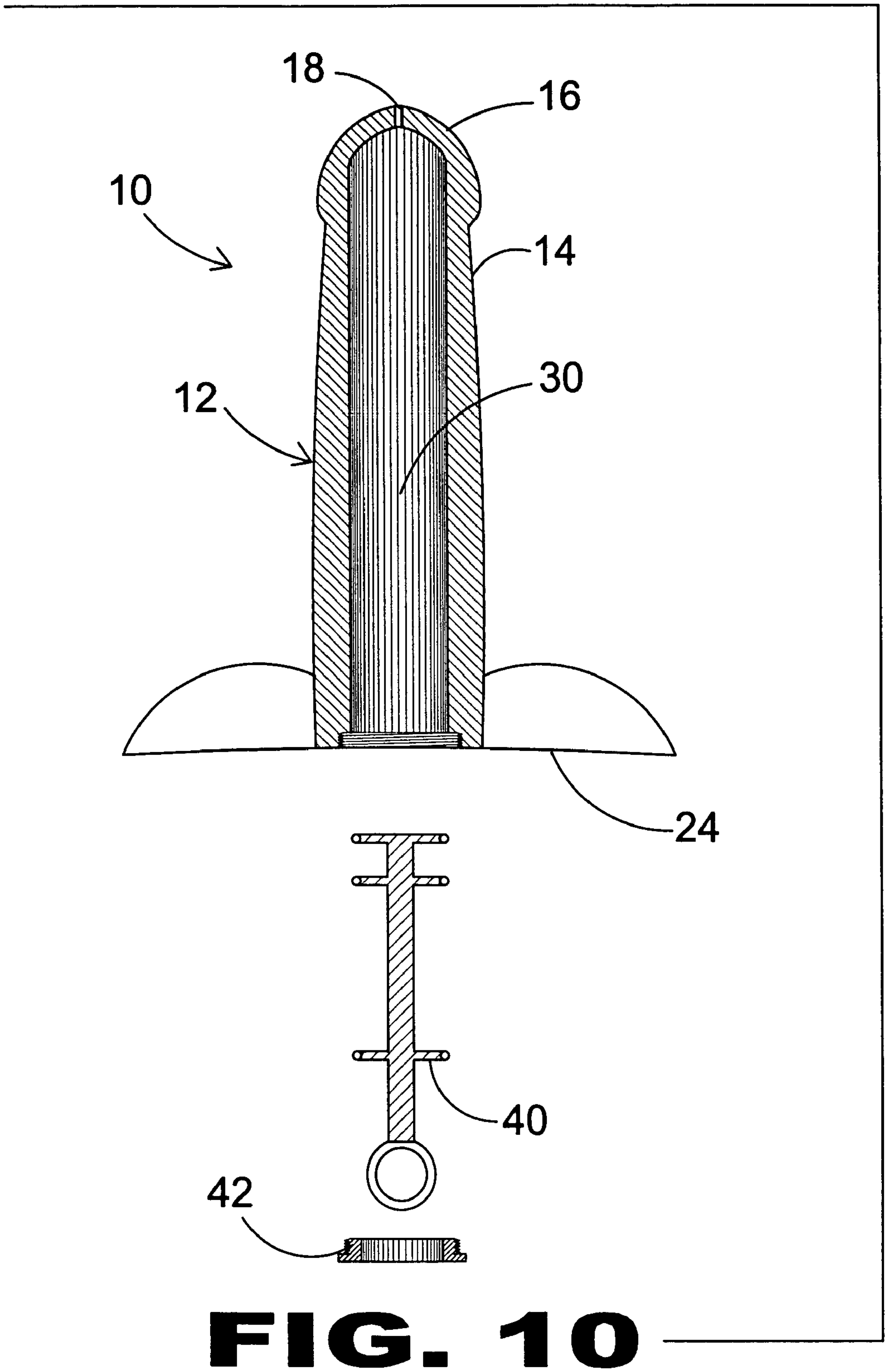
FIG. 10 is an exploded view of the alternate embodiment of the lubricating sexual aid of the present invention.

FIG. 10 is an exploded view of the alternate embodiment of the lubricating sexual aid of the present invention. The lubricating sexual aid 10 is preferably formed in the shape of a penis. The aid 10 includes the body 12 having the handle 24 positioned at a base end thereof. The body 12 includes the shaft 14 and the head 16. The shaft 14 includes the bore 20 extending along the entire length of thereof. The head 16 is positioned at the distal end of the shaft 14 opposite the handle 24. The head 16 is substantially hemispherical in shape and includes the egress aperture 18 positioned at an apex thereof. The bore 20 extending through the shaft 14 forms the reservoir 30 for receiving the lubricant 36 therein. The lubricant is preferably K-Y JELLY™. However, any lubricant that is approved for safe use and that will not irritate or harm a human may be used with the sexual aid 10 if the present invention.

Upon the lubricant being received within the reservoir 30, a plunger 40 is received within the bore 20. A plunger cap 42 secures the plunger 40 within the bore 20. The plunger 40 includes a flat head 44 for applying a pressure to the lubricant 36 contained in the reservoir 30. The plunger further includes the ring 41 for receiving at least one of a finger and a thumb therethrough. Upon the ring 41 receiving the at least one of the finger and thumb, the plunger 40 is move along the interior of the bore 20 and the flat head 44 applies pressure to the lubricant 36 thereby forcing the lubricant 36 out from the reservoir 30 through the egress aperture 18. When the plunger 40 is depressed in a direction illustrated by the arrow labeled with the reference numeral 34, the lubricant 36 is forced out from the reservoir 30 through the egress aperture 18. The plunger 40 retracts when the reservoir 32 is refilled thus returning it to full status.

The sexual aid 10 of the present invention is selectively insertable into an orifice of the human body such as the vagina or anus in order to stimulate sexual pleasure of the user. The user is able to hold and manipulate the aid 10 by the handle 24 which is formed in a shape substantially similar to a pair of testicles. This is shown for exemplary purpose only and the handle 24 may be formed in any shape that is comfortable for the user to grip and use the aid 10 of the present invention. It is desirable to apply a lubricant to a sexual aid in order to minimize irritation therby increasing the level of pleasure provided by the sexual aid. Thus, the lubricating sexual aid 10 of the present invention allows for a user to deposit the lubricant 36 within the orifice while the aid 10 is being used. Upon insertion of the lubricating sexual aid 10, the user depresses the plunger 40 which causes the lubricant 36 to exit through the egress aperture 18 of the head 16. The lubricant 36 contacts the walls of the orifice and is caused to be spread about an exterior surface of the head 16 and shaft 14 of the body 12 thereby reducing and/or eliminating any friction typically associated with repeated removal and insertion of the aid 10.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A lubricating insertable sexual aid comprising:

a) a shaft having a throughbore extending therethrough for retaining a lubricant therein;

b) A head having an egress aperture extending through a tip thereof removeably connected to a first end of said shaft; and c) Means received within said throughbore at an end opposite said head for dispensing said lubricant; wherein upon insertion into an orifice and activation of said dispensing means, said dispensing means exerts a pressure on said lubricant thereby causing said lubricant to be output via said egress aperture and to be evenly distributed over an exterior surface of each of said head and shaft, said dispensing means includes a plunger and piston, wherein said piston is received within said throughbore and said plunger causes said piston to move along said throughbore thereby exerting a pressure on said lubricant and forcing said lubricant through said egress aperture and wherein said plunger is an air-pressure plunger having an interior and exterior member thereof, wherein each of the interior member and the exterior member include a one way valve for allowing air to fill an empty space and upon depressing said plunger, a first one way valve on said exterior member closes and forces air through a second one-way value on said interior member thereby exerting a pressure on said piston.

2. The apparatus as recited in claim 1, wherein said shaft is substantially cylindrical in shape.

3. The apparatus as recited in claim 1, wherein said head is hemispherical in shape.

4. The apparatus as recited in claim 1, wherein said piston includes a plurality of rollers extending around a periphery thereof.

5. The apparatus as recited in claim 1, wherein said dispensing means is a plunger having a ring at a first end for receiving at least one of a finger and thumb therethough and a flat head at an end opposite said ring, wherein said flat head is received within said throughbore for exerting a pressure on said lubricant contained therein.

6. The apparatus as recited in claim 5, further comprising a plunger cap removeably positioned within said throughbore for maintaining said plunger in a stable position allowing said flat head to exert even pressure about said lubricant.

7. The apparatus as recited in claim 1, further comprising a handle for griping and maneuvering said aid into and out of an orifice in the human body.

8. The apparatus as recited in claim 1, wherein said orifice includes at least one of a vagina and anus.

9. The apparatus as recited in claim 1, wherein said head is screwably connected to said shaft for easy removal thereof.

10. The apparatus as recited in claim 1, wherein said aid is shaped substantially similar to a penis.

* * * * *